(12) United States Patent
Wheelock et al.

(10) Patent No.: US 8,362,258 B2
(45) Date of Patent: Jan. 29, 2013

(54) TRANSITION METAL MEDIATED OXIDATION OF HETERO ATOMS IN ORGANIC MOLECULES COORDINATED TO TRANSITION METALS

(75) Inventors: Kenneth S. Wheelock, Pittsfield, MA (US); Louis A. Piccone, Dalton, MA (US)

(73) Assignee: Praktikatalyst Pharma LLC, Pittsfield, MA (US)

( * ) Notice: Subject to any disclaimer, the term of this patent is extended or adjusted under 35 U.S.C. 154(b) by 699 days.

(21) Appl. No.: 12/459,757

(22) Filed: Jul. 7, 2009

(65) Prior Publication Data

US 2009/0274755 A1     Nov. 5, 2009

Related U.S. Application Data

(63) Continuation of application No. 11/434,559, filed on May 15, 2006, now Pat. No. 7,579,476.

(60) Provisional application No. 60/776,563, filed on Feb. 24, 2006.

(51) Int. Cl.
*C07D 401/12* (2006.01)
(52) U.S. Cl. .................................................. 546/273.7
(58) Field of Classification Search ............... 546/273.7
See application file for complete search history.

(56) References Cited

U.S. PATENT DOCUMENTS

| 5,948,789 | A  | * | 9/1999 | Larsson et al. | 514/299 |
| 6,369,085 | B1 | * | 4/2002 | Cotton et al. | 514/338 |
| 6,875,872 | B1 | * | 4/2005 | Lindberg et al. | 546/273.7 |

* cited by examiner

*Primary Examiner* — Patricia Morris
(74) *Attorney, Agent, or Firm* — Kenneth S. Wheelock

(57) ABSTRACT

The present invention is directed to a process for the catalytic oxidation of the thioether 5-methoxy-2-((4-methoxy-3,5-dimethyl-2-pyridinyl)methyl)methylthio)-1H-benzimidazole to its sulfoxide: 5-methoxy-2-((4-methoxy-3,5-dimethyl-2-pyridinyl) methyl)methylsulfinyl)-1H-benzimidazole comprising: reacting the thioether with: 1) a transition metal catalyst; and, 2) an oxygen source; wherein the thioether is oxidized to a sulfoxide and wherein one of either the R and S enantiomers is formed to an enantiomeric excess.

8 Claims, No Drawings

TRANSITION METAL MEDIATED OXIDATION OF HETERO ATOMS IN ORGANIC MOLECULES COORDINATED TO TRANSITION METALS

CROSS-REFERENCE TO RELATED APPLICATIONS

This application is a Continuation Application of U.S. Ser. No. 11/434,559 filed May 15, 2006, now U.S. Pat. No. 7,579,479, which claims priority to U.S. Provisional Patent Application No. 60/776,563 filed Feb. 24, 2006.

FIELD OF THE INVENTION

The present invention is directed to a process for the direct or catalytic oxidation of the thioether 5-methoxy-2-((4-methoxy-3,5-dimethyl-2-pyridinyl)methyl)methylthio)-1H-benzimidazole, to its sulfoxide: 5-methoxy-2-((4-methoxy-3,5-dimethyl-2-pyridinyl)methyl)methylsulfinyl)-1H-benzimidazole comprising: reacting the thioether with: 1) a transition metal compound; and, 2) an oxygen source; wherein the thioether is oxidized to a sulfoxide and wherein one of either the R and S enantiomers is formed to an enantiomeric excess.

The present invention is also directed to pharmaceutical dosage forms containing the sulfoxide for use in treating patients medical conditions in need of such benzmidizole active agents.

The present invention is still yet further directed to a kit for the administration of a pharmaceutically active agent comprising: a) a pharmaceutically active agent as a dosage form selected from pills, tablets, capsules, liquids and powders; b) an information guide describing the dosage form and how to use the dosage form; c) a package for containing a) and b).

BACKGROUND OF THE INVENTION

Many useful organic compounds contain hetero-atoms, e.g oxygen, sulfur, selenium, tellurium, nitrogen, phosphorus, arsenic, and antimony. Some of the simplest hetero-atom compounds are obtained by the insertion of a hetero-atom between the carbon and the hydrogen of hydrocarbon structures, e.g. oxygen inserted into one of the carbon hydrogen bonds of methane generates methanol, an alcohol. Such substitutions produce the rich and varied structural chemistry of carbon compounds. When the hetero-atom is not oxygen, e.g. sulfur, selenium, tellurium, nitrogen, phosphorus, arsenic, and antimony, lone pair electrons on the hetero-atom may participate in the formation of a dative bond to an oxygen atom creating a correlative oxidized product. In the case of an organic amine the correlative oxidized product is an amine N-oxide; phosphine oxides are similarly derived from phosphines. In the case of organic sulfur compounds, the two lone electron pairs resident on the sulfur atom of a thioether will participate in such an oxidation in a stepwise fashion forming first a sulfoxide and then a sulfone.

Frequently, the correlative oxidation product acquires new structural properties as a consequence of being oxidized. Tertiary amines of the formula $R^aR^bR^cN$ when oxidized to form the N-oxide, $R^aR^bR^cNO$, exhibit the same type of stereochemistry as carbon compounds where when a given carbon atom in a structure is substituted by four different substituents, optical isomers isomers are generated, i.e. enantiomeric isomers. While it is possible to surmise that non-symmetric tertiary amines may exist as optical isomers, the well known interconversion of structures through the reversible umbrellation of the nitrogen atom rapidly moots such a stereochemical question (the term non-symmetric is used herein in an inclusive fashion to encompass the more specific terms dissymetric and asymmetric). This is not the case for organic sulfur compounds, where the lone electron pair on sulfur is not labile in the fashion of nitrogen, it does not undergo interconversion between enantiomers. Thus the first oxidation of a non-symmetric thioether, e.g. $R^aR^bS$, leads to a sulfur oxide that exists in enantiomeric forms because the lone electron pair of the surfer is stereochemically significant, i.e. it is not stereochemically labile in the sense that the molecule rapidly undergoes the umbrellation typical of the lone pair on the nitrogen atom of amines. Further oxidation of the sulfoxide to the sulfone destroys the optical isomerism because now the sulfur atom has two identical substituents, the two oxygen atoms of the sulfone.

Many of the N-oxide compounds, the sulfoxides and the like have significant uses regardless of their stereochemistry. For example, tertiary N-oxides are excellent oxidation inhibitors in polymers. When thermoplastic polymers are processed at high temperatures such as those occurring in extrusion where the polymer must be molten, when one of the substituents of the tertiary amine is a methyl group the tertiary N-oxide can under go an elimination reaction to produce a substituted hydroxylamine compound in situ that acts to prevent thermal degradation of the polymer.

In contrast, it has been found that many drugs exist in enantiomeric or mesomeric forms and that one optical isomer is pharmaceutically more active than other isomers. As long as some of the enantiomeric forms of these compounds are biologically inert they present only economic issues in the manufacture of the active ingredient. However, it has occasionally been found that while one enantiomeric isomer of a pharmaceutically active compound is beneficial the other, or others, may be detrimental. This leads to problems of stereochemical control in order to isolate the desired therapeutically active form of the molecule.

The conversion of amines in the synthesis of many drugs or to complex methods of purifying the active ingredients, phosphines, thioethers and the like to their correlative oxides by free radical oxidation such as the use of atmospheric oxygen being bubbled through a liquid reaction medium or using peroxide compounds, e.g. hydrogen peroxide or peracetic acid, creates just these sorts of problems, introducing a center of optical isomerism into the converted molecule, i.e. a chiral center, and creating enantiomers where one of the enantiomers is more pharmaceutically active than the other enantiomers.

Coordination complexes of transition metals may exist in a variety of isomeric forms broadly characterized as positional isomerism, i.e. the same set of atoms but a different set of bonds, or stereoisomerism, i.e. the same set of atoms and bonds but different symmetries. Broadly the types of positional isomerism in coordination complexes are:
1) linkage isomerism exists when the coordinating ligand may bond to the transition metal through more than one atom, example: complexes of ONO ($NO_2$), when bonded through the nitrogen the complex is a nitro complex and when bonded through the oxygen the complex is a nitrito complex;
2) coordination isomerism exists when differing central metal ions can exchanged between differing sets of ligands, e.g. $(Cr(NH_3)_6) (Co(CN)_6)$ versus $(Co(NH_3)_6) (Cr(CN)_6)$;
3) ligand isomerism exists when the group bonding to the central metal ion can be substituted into different positions of the ligand molecule, e.g. $(Co(1,2\text{-diaminopropane})^3)^{+3}$ versus. $(Co(1,3\text{-diaminopropane})^3)^{+3}$;

4) solvation isomerism (or more specifically with $H_2O$, hydration isomerism) exists when the solvent is coordinated versus being part of the crystal structure as in water of hydration, e.g. $(Cr(H_2O)_6)$ $Cl_3$ versus $(Cr(H_2O)_5Cl)$ $Cl_2$—$H_2O$;

5) ionization isomerism exists when species are exchanged between the coordination sphere and simple ions, e.g. (Pt $(NH_3)_4(OH)_2$) $SO_4$ versus $Pt(NH_3)_4SO_4$) $(OH)_2$; and 6) polymerism isomerism exists when the molecular weights are different but the empirical weights are the same, e.g. $(Pt(NH_3)_2Cl_2)_n$ versus $(Pt(NH_3)_4)$ $(PtCl_4)$.

Stereoisomerism broadly exists in two major classes:
1) geometric isomerism exemplified by cis trans isomerism in square planar or octahedral complexes; and
2) optical isomerism.

Optical isomerism as it exists in transition metal complexes is similar to the optical isomerism observed in carbon compounds. A simplified view of optical isomerism in transition metal chemistry is when there is no center or plane of symmetry passing through the central metal ion of a transition metal compound or complex and the ion, compound or molecule may exist in two or more forms that possess an identical chemical formula and molecular weight but wherein the differing forms of the molecule can not be interconverted by rotation of substituent groups around molecular bonds. Thus the molecules exist in so-called enantiomeric isomers or if two or more centers of asymmetry exist in the molecule, diastereomeric isomers. The terms dissymetric and asymmetric have acquired a particularly specific meaning in the field of stereochemistry; as used herein the term non-symmetric will be used herein to refer generally and inclusively to those chemical structures that would properly be more specifically described either as dissymetric or asymmetric. Non-symmetric complexes of transition metals have been found to be useful in the synthesis or preparation enantiomeric organic compounds, either by more or less standard chemical reactions or reactions that have been catalyzed either by homogeneous or heterogeneous catalysts.

SUMMARY OF THE INVENTION

The present invention is directed to a process for the direct or catalytic oxidation of the thioether 5-methoxy-2-((4-methoxy-3,5-dimethyl-2-pyridinyl)methyl)methylthio)-1H-benzimidazole to its sulfoxide: 5-methoxy-2-((4-methoxy-3,5-dimethyl-2-pyridinyl)methyl)methylsulfinyl)-1H-benzimidazole comprising: reacting the thioether with: 1) a transition metal compound; and, 2) an oxygen source; wherein the thioether is oxidized to a sulfoxide and wherein one of either the R and S enantiomers is formed to an enantiomeric excess.

The present invention is also directed to a pharmaceutical preparation comprising: (a) an alkaline reacting core comprising an acid-labile pharmaceutically active substance and an alkaline reacting compound different from said active substance, an alkaline salt of an acid labile pharmaceutically active substance, or an alkaline salt of an acid labile pharmaceutically active substance and an alkaline reacting compound different from said active substance; (b) an inert subcoating which rapidly dissolves or disintegrates in water disposed on said core region, said subcoating comprising one or more layers comprising materials selected from the group consisting of tablet excipients, film-forming compounds and alkaline compounds; and, (c) an enteric coating layer surrounding said subcoating layer, wherein the subcoating layer isolates the alkaline reacting core from the enteric coating layer such that the stability of the preparation is enhanced and, wherein the acid labile pharmaceutically active substance is a benzimidazole compound and is made according to a process wherein the sulfoxide: 5-methoxy-2-((4-methoxy-3,5-dimethyl-2-pyridinyl)methyl)methylsulfinyl)-1H-benzimidazole is catalytically converted from the thioether 5-methoxy-2-((4-methoxy-3,5-dimethyl-2-pyridinyl)methyl)methylthio)-1H-benzimidazole by: reacting the thioether with: 1) a transition metal catalyst; and, 2) an oxygen source; wherein the thioether is oxidized to a sulfoxide and wherein one of either the R and S enantiomers is formed to an enantiomeric excess.

DETAILED DESCRIPTION OF THE PREFERRED EMBODIMENTS

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, various salts of benzimidazole compounds including, but not limited to the sodium, and potassium salts, acetate, formate and benzoate derivatives of alcohol and amine functional groups in the compounds of the present invention. Also, for purposes of the present invention the term prodrug includes the all physical forms of an active agent including crystalline and amorphous.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" is intended to include an amount of a compound of the present invention or an amount of the combination of compounds claimed effective to alleviate a patient demonstrating a need for $H_2$ antanogists or the active agents which are the subject of the present invention.

For purposes of the present invention the term "coordination compound" means those compounds formed by the union of a metal ion (usually a transition metal) with a non-metallic ion or molecule called a "ligand". The ligand may be either positively or negatively charged or it may be a molecule of water or ammonia The most common metal ions are transition metal ions including by way of example, cobalt, platinum, iron, copper, nickel and ruthenium which form highly stable compounds. The total number of bonds linking the metal to the ligand is called its "coordination number". It is usually 2, 4, or 6 but often depends on the type of ligand involved. All ligands have electron pairs on the coordinating atom that can be either donated to or shared with the metal ions. The metal ion acts as a Lewis acid (electron acceptor), and the ligand as a Lewis base (electron donor). The charge on the complex ion is the sum of the charges on the metal ion and the ligands. Such coordination compounds may participate in direct reactions for example such as oxidation or reduction or they may act as catalysts to catalyze oxidation or reduction. The chemical reactions or transformations occurring by means of using the transition metal compounds herein described may occur as direct reactions including but not limited to oxidation, reduction, metathesis, exchange, addition, elimination, or rearrangement; or they may occur as catalyzed reactions where the transition metal compounds herein described function as catalysts, either homogeneously or heterogenerously. Where the term compound is used herein or in the appended claims, the word is intended to cover the use of the compound either as a stoichiometric reactant or as a catalyst to achieve the chemical transformation specified. As used herein, the word direct means participation in a chemical reaction or transformation on a stoichiometric basis. As used herein the word catalytic or the various grammatical variants thereof means participation in a chemical reaction on a non-stoichiometric basis. As used herein the phrase "oxygen source" includes but is not limited to the group consisting of peracids, hydrogen peroxide, dimethydioxirane and molecular oxygen The term "host" or "patient" according to the present invention includes all mammals in particular all animals and more particularly humans, household animals such as dogs and cats, farm animals, such as goats and sheep and livestock such as cows and pigs.

The combination of compounds is preferably a synergistic combination. Synergy, as described for example by Chou and Talalay, Adv. Enzyme Regul. 1984, 22, 27-55, occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased $H_2$ antagonism, or some other beneficial effect of the combination compared with the individual components.

S-5-methoxy-2-((4-methoxy-3,5-dimethyl-2-pyridinyl) methyl)methylsulfinyl)-1H-benzimidazole is a known pharmaceutically active agent generically know as s—O—M—E—P—R—A—Z—O—L—E and sold by the Astra Zeneca company under several tradenames including P—R—I—L—O—S—E—C. Methods of this compound's manufacture are well known in the art. U.S. Pat. No. 6,875,872, filed on Oct. 16, 2000, assigned to Astra Zeneca and incorporated herein by reference in its entirety as though set forth in full, describes benzimidizole compounds which are relevant to the present invention.

Benzimidizole compounds according to the present invention may be used in conjunction with other pharmaceutically active agents including but not limited to antibiotics and non-steroidal anti-inflammatory agents.

We have now found that coordinating an organic precursor to specific transition metal ions forming a non-symmetric or chiral coordination complex allows for compositions and processes, and specifically a process where the stereochemistry of subsequent reactions of a subsequently coordinated pharmaceutical precursor may be controlled. Further we have now found that this may be accomplished by using non-symmetric or chiral complexes of transition metal ions. This may be accomplished in at least one of at least two methods involving non-symmetric or chiral transition metal complexes:

1) reaction of a transition metal complex with an organic precursor to form a chiral transition metal complex followed by reaction of the coordinated organic precursor to yield a coordinated ligand that is itself non-symmetric or chiral when dissociated from the non-symmetric or chiral transition metal complex; and 2) reaction of a non-symmetric or chiral transition metal complex with an organic precursor to form a chiral transition metal complex followed by reaction of the coordinated organic precursor to yield a coordinated ligand that is itself non-symmetric or chiral when dissociated from the non-symmetric or chiral transition metal complex.

When such non-symmetric or chiral complexes are combined with substrates that may react to form enantiomers, the reactions of coordinated ligands that may be pharmaceutical precursors leads to products having a more or less controlled stereochemistry, i.e. certain desired compounds may be produced in enantiomeric excess. As used herein the term enantiomeric excess refers to that synthetic result obtained from a reaction where out of a manifold of two or more enantiomeric compounds that are the reaction product of a given reaction, one enantiomer of the manifold of reaction products is present in the mixture in excess of the other on a weight percent basis, a volume percent basis or a mole percent basis. As used herein the term chiral is used in its generally accepted sense.

The present invention also provides for a means of recovering these chemically modified coordinated species after they have been reacted.

Thus the present invention provides for a process for the direct or catalytic oxidation of a thioether comprising:
    reacting:

a) a thioether having the formula $R^1SR^2$ where $R^1$ and $R^2$ are each independently monovalent organic radicals containing from six to thirty carbon atoms;
b) a transition metal catalyst; and
c) an oxygen source whereby said thioether is oxidized to a sulfoxide. The radicals $R^1$ and $R^2$ may be any monovalent organic radical comprising carbon and hydrogen and having from six to thirty carbon atoms, optionally substituted with one or more heteroatoms selected from the group consisting O, S, Se, Te, N, P As and Sb where in the hydrogen atoms may be substituted by halogens selected from the group consisting of fluorine, chlorine, bromine and iodine.

The present invention further provides for a process wherein the transition metal compound or catalyst is a coordination complex of said transition metal (as used herein the phrase transition metal catalyst and transition metal coordination complex and word variants thereof may be used interchangeably to denote a transition metal catalyst). The present invention further provides for a process of claim 2 wherein said coordination complex of said transition metal comprises one or more ligands selected from the group consisting of monodentate, bidentate tridentate or polydentate ammines, di-ammines, polyamines, phosphines, di-phosphines and polyphosphines. More particularly the present invention provides for a process wherein said ligand is 2(S), 3(S)-bis(diphenylphosphino)butane. More particularly the present invention provides for a process wherein said complex additionally comprises cyclopentadienyl. Most particularly the present invention provides for a process where said thioether is 5-methoxy-2-((4-methoxy-3,5-dimethyl-2-pyridinyl)methyl)methylthio)-1H-benzimidazole and wherein said sulfoxide is 5-methoxy-2-((4-methoxy-3,5-dimethyl-2-pyridinyl)methyl)methylsulfinyl)-1H-benzimidazole.

The process of the present invention involves the preparation of a transition metal complex of a transition metal that is coordinatively unsaturated and that will further react with at least one additional coordinating ligand, the substrate ligand. Upon forming a coordination complex with the substrate ligand the transition metal complex is preferably non-symmetric or chiral. The coordinated substrate ligand is subsequently chemically modified while coordinated to the transition metal complex so that the substrate ligand adopts a preferred stereochemistry when it is reacted while coordinated. Preferably the reaction is an oxidation reaction. The chemically modified coordinated substrate ligand is dissociated from the transition metal complex by reaction. The transition metal compound or complex may be re-used in a catalytic cycle. The chemically modified substrate ligand is isolated and used in a preferred embodiment as a pharmaceutical.

Almost all of the transition metals of the third, fourth and fifth periods of the periodic table form coordination complexes and under the appropriate circumstances most of these metals are capable of acting either as homogeneous or heterogeneous catalysts. The highest levels of stereochemical and kinetic control are frequently accomplished under conditions typically characterized as homogeneous catalysis. In its simplest definition a catalyst is a substance that changes the reaction rate of a chemical reaction without participating in the overall reaction. As with all simple definitions this oversimplifies what actually occurs on a microscopic scale, so that species that may be characterized as a catalyst at one level of abstraction actually are participants in the reaction at a finer level of resolution. These species that exit the reaction sequence in the form in which they entered the sequence are formally catalysts but they have undergone a series of chemical changes or transformations between the two endpoints of the process. As used herein the term "mediated" is used to describe the universe of chemical transformations involving a transition metal coordination complex where the transition metal may or may not be recycled and re-used to effect a transformation, e.g. oxidation, reduction, addition or elimination reaction, on a chemical substrate of some type, here more particularly a pharmaceutical precursor. Thus the term meditated includes but is not limited to ordinary chemical reactions and catalytic reactions, both homogeneous and heterogeneous catalytic reactions.

The term transition metal includes the chemical elements having an atomic number ranging from 21-30, 39-48, 57-80 and 89-103, inclusive. This range includes the lanthanide and actinide series of elements, 57-71 and 89-103 respectively. More specifically the transition metals used to accomplish the processes of the present invention are the transition metals of Groups VIb and VIII of the periodic table, elements having atomic numbers 24, 42, 74, 26, 27, 28, 44, 45, 46, 76, 77 and 78. Most specifically, the elements used to accomplish the process of the present invention have atomic numbers 24, 74, 44, 45, 46, 77 and 78, i.e. Cr, W, Ru, Rh, Pd, Ir and Pt.

These transition metals are used as their coordination complexes, i.e. in their ionic form as the reaction product of a transition metal salt, typically a halide, i.e. fluoride, chloride, bromide or iodide with coordinating ligands, either chiral or non-chiral coordinating ligands that are typically ammines, di-ammines, polyamines, phosphines, di-phosphines, polyphosphines, whether monodentate, bidentate tridentate or polydentate. These coordination complexes may or may not be further reacted with either the same or other chiral or non-chiral coordinating ligands, typically ammines, di-ammines, polyamines, phosphines, di-phosphines, polyphosphines, whether monodentate, bidentate tridentate or polydentate. The resulting reaction product is a reactive or coordinatively unsaturated coordination complex that is preferably non-symmetric or chiral that will further coordinate or complex an additional molecular specie or species, an organic ligand or pharmaceutical precursor which after coordination is reacted with a reagent to oxidize, reduce, add chemical moieties to or eliminate chemical moieties from the coordinated organic or pharmaceutical precursor. Because most coordination complexes with transition metals involve the formation of a bond between the coordinating species or ligand and the transition metal, this bond is most easily formed when the coordinating species (hereinafter ligand) has at least one lone pair of electrons and the coordinating transition metal has a vacant outer orbital, typically a valence d, s or p orbital. Ligands with at least one lone pair of electrons typically incorporate a hetero-atom selected from the group consisting of N, P, As, Sb, O, S, Se, or Te, although the pi-electrons of olefinic, acetylenic and aromatic molecules can also participate in this type of bonding, acting as a ligand. Usually these hetero-atoms are the locus of the lone pair of electrons and thus are not fully oxidized in terms of the available oxidation states of the hetero-atom.

In preparing the coordinatively unsaturated coordination complex of a transition metal ion comprising ammine and/or phosphine ligands it may be useful to change the oxidation state of the transition metal either by oxidizing the complex or reducing it in order to create the coordinative unsaturation. Oxidizing agents as hereinafter listed for reaction of the substrate ligand may be used to oxidize the complex. Reducing agents may be employed to lower the oxidation state, a preferred reducing agent is hydrazine. Such techniques are routine in the art.

Several different reactants may be utilized to effect chemical structure change of the coordinated ligand or organic precursor. For example acid halides of the general formula:

where $R^d$ is a monovalent organic radical, C(O) is the carbonyl functionality associated with organic carboxylic acids and X is a halogen selected from the group consisting of fluorine, chlorine, bromine, and iodine, with chlorine and bromine preferred and chlorine particularly preferred.

Another example of a reaction of a coordinated molecule may involve the use acid anhydrides of the general formula:

where $R^d$ is a monovalent organic radical, C (O) is the carbonyl functionality associated with organic carboxylic acids and $R^e$ is the same or a different monovalent organic radical, i.e. differing from $R^d$.

Coordinated ligands may be oxidized by various reactive oxygen species such as peroxyacids, molecular oxygen, hydrogen peroxide, and molecular species containing reactive oxygen.

Peracid Oxygen Source

Peracids or peroxy acids are typically organic acids having the general formula:

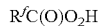

where $R^f$ is typically a monvalent organic radical or hydrogen and C(O) is the carbonyl functionality associated with organic carboxylic acids. Many of the so-called peroxy acids are commercially available, e.g. peracetic acid, $CH_3C(O)O_2H$, peroxy benzoic acid where the $R^f$ radical is $C_6H_5$, peroxy formic acid, $HC(O)O_2H$, trichloroperacetic acid, $CCl_3C(O)O_2H$ and 3-chloroperbenzoic acid (meta-chloroperoxybenzoic acid) as a non-limiting list. Inorganic peracids are also known and may be useful, e.g. peroxy monosulfuric acid $H_2SO_3(O_2)$ and peroxy disulfiric acid $H_2(SO_3)_2O_2$.

Molecular Oxygen

The reaction may be conducted in the presence of atmospheric oxygen. Atmospheric oxygen, O2, may be bubbled through the reaction medium or pure oxygen (commercially available either as the gas under pressure or as the super-cooled liquid) may be used.

Hydrogen Peroxide Oxygen Source

Instead of atmospheric oxygen being introduced into the reaction medium, any source of dissolved or aqueous hydrogen peroxide can be used including those containing 3-100 percent hydrogen peroxide. Preferably the hydrogen peroxide is between about 20-70 weight percent, more preferably between 45-70 weight percent active hydrogen peroxide. Due to the presence of the solvent in the present process, more concentrated hydrogen peroxide can be used without presenting difficulties in stirring the reaction mixture.

A useful amount of hydrogen peroxide should be at least a stoichiometric amount. The range is typically between about 1-5 moles of hydrogen peroxide, more preferably 1-1.5 mole of hydrogen peroxide, per mole of tertiary amine. A highly preferred amount is about 1.05-1.3 moles of hydrogen peroxide, and especially about 1.1-1.2 moles, of hydrogen peroxide per mole of compound to be oxidized. Any excess hydrogen peroxide remaining after the reaction can be destroyed by the addition of a reducing agent, for example, sodium sulfite, sodium thiosulfate, and/or sodium thiosulfite. Additionally, enzymes known in the art such as those available from Novo Nordisk under the tradename Catazyme, including product 50L, have been shown to be efficient for destroying any excess hydrogen peroxide remaining.

Molecular Reactive Oxygen Sources

A reactive source of oxygen for the oxygenation or oxidation reactions herein disclosed is dimethyldioxirane (DMD): $(CH_3)_2C(O_2)$, a molecule possessing a three membered ring composed of two oxygens and one carbon atom and substituted with two methyl groups on the ring carbon atom. Despite its highly reactive nature chemically, dimethyldioxirane is unexpectedly selective in its ability to act as a selective electrophilic oxygen transfer reagent. DMD may be used in epoxidation reactions, and is especially useful in the selective epoxidation of organo-transition metal complexes such as polyene complexes. DMD has also been used to change the functionality of hydrido-siloxanes by inserting an oxygen atom in the silicon hydrogen bond. A particular advantage of using DMD as a source of oxygen is that acetone, $(CH_3)_2C(O)$, is the only product after complete oxygen transfer, simplifying subsequent work-up because of its volatility.

Choice of Solvent

When it is desired to separate the reaction products by azeotropic distillation, the organic solvent used in the present invention may be any organic liquid in which the organic hetero-compound and its correlative oxidized product are soluble at the reaction temperature and which may or may not be capable of forming an azeotrope with water. However, to avoid the danger of explosion, this solvent may be substantially inert. In a preferred embodiment of the invention, the solvent is capable of maintaining the reaction mixture fluid and stirrable without being used in an amount that would reduce the solids content of the reaction mixture below about 15% by weight, preferably below about 30% by weight. Excellent results can be achieved at a solids level of about 50% by weight. Based on cost and availability, as well as effectiveness, the preferred solvents for use in the process are the lower alkyl alcohols, such as the C1-C8 alcohols, and especially the C1-C4 alcohols, containing one or more hydroxyl groups. Exemplary alcohols include methanol, ethanol, 1-propanol, 2-propanol, 1-butanol, 2-butanol, 1-pentanol, 2-pentanol, 3-pentanol, tert-butyl alcohol, 1-hexanol, 2-hexanol, 3-hexanol, 2-methyl-1-propanol, 2-methyl-2-propanol, tert-amyl alcohol, 2-methyl-1-butanol, 3-methyl-1-butanol, 3-methyl-2-butanol, neopentyl alcohol, 2,3-dimethyl-2-butanol, 3,3-dimethyl-2-butanol, 1-hexyl alcohol, 2-hexanol, 3-hexanol, and the like as well as various mixtures thereof. Especially preferred solvents include 1-propyl alcohol, 2-propyl alcohol, 1-butanol, and 2-butanol.

The solvent may optionally contain another solvent such as an aliphatic, cycloaliphatic, or aromatic hydrocarbon such as hexane, isohexane, heptane, 2-ethylhexane, octane, isooctane, cyclohexane, cyclooctane, toluene, or the like, or a halohydrocarbon such as chlorobenzene, dichlorobenzene, bromobenzene, chlorotoluene, 2,4-dichlorotoluene, and the like. Ester solvents are also useful as a co-solvent and exemplary ester solvents include methyl acetate, ethyl acetate, isopropyl acetate, butyl acetate, sec-butyl acetate, t-butyl acetate, isobutyl acetate, amyl acetate, and the corresponding propionates, butyrates, and valerates. When the optional co-solvent is used, the amount is generally limited to an amount up to about 25% (e.g., 1-25%) by weight based on the weight of the polar solvent. The use of the non-polar solvent reduces the solubility of the tertiary amine and/or amine oxide in the reaction mixture.

The present process also includes the use of a promoter for the oxidation of the hetero-atom especially when the hetero-atom is a nitrogen. Preferred promoters include lower organic acids that are capable of removal by distillation from the reaction mixture at the completion of the oxidation. Preferred acids include: formic acid, acetic acid, and propionic acid with acetic acid being especially preferred. Other organic carboxylic acids, such as diethylenetriaminepentaacetic acid or ethylenediaminetetracarboxylic acid, are also useful. Other promoters include ammonium carbonate, ammonium bicarbonate, and ammonium carbamate, as well as mixtures of promoters. Carbon dioxide and aluminum are also effective promoters.

The amount of promoter can vary over a wide range. It is required that the amount of promoter in the reaction mixture, in whatever form it exists, be an amount which causes the reaction to proceed at a faster rate than the rate achieved without the addition of the promoter. In other words there should be at least a catalytic amount of the promoter. Useful concentrations of the promoter include from about 0.001-10 weight percent based on weight of the hetero-atom compound precursor. A preferred concentration is about 0.005-1 weight percent. A more preferred concentration is about 0.01-0.8 weight percent. When carbon dioxide is added as a promoter, it may be added as a blanket over the reaction mixture, or more preferably, the carbon dioxide can be dissolved in the aqueous hydrogen peroxide and/or in the solvent.

The reaction can be conducted over a wide temperature range depending on the substrate. The temperature should be high enough to cause the reaction to proceed at a reasonable rate but not so high as to lead to decomposition of the reactants or products. A useful temperature range is from about −30 to 140° C. A more preferred temperature range is about −20 to 140° C. A still more preferred temperature range is about 45-130° C. For oxidation of nitrogenous species most preferably the reaction is conducted at about 45-110° C. In this temperature range the reaction is quite rapid and is normally complete in less than about 30 hours, generally less than about 20 hours. Excellent results have been achieved at about 55-90° C. For oxidation of sulfur species temperature in the range −30 to 30° C. are preferred.

In one embodiment, the process of the invention is conducted by adding the aqueous hydrogen peroxide to a solution of the tertiary amine in the solvent containing the promoter. The organic solvent is generally present throughout the reaction, although the amount present at any point during the reaction is quite flexible. The organic solvent may be minimized during initiation of the reaction and then gradually added during the course of the reaction to maintain the reaction mixture fluid and stirrable. Alternatively, the organic solvent may be entirely added at the beginning of the reaction or may be added later during the course of the reaction provided that the solvent is present for the azeotropic removal of the water from the aqueous hydrogen peroxide. The hydrogen peroxide is preferably added at a controlled rate such that the temperature is preferably maintained within the ranges as previously discussed. Cooling may become necessary to maintain the temperature within the desired range. The addition rate of the hydrogen peroxide is, preferably, such that a large accumulation of unreacted hydrogen peroxide is not present at any particular moment in time. The reaction temperature is maintained within the temperature range until the oxidation is substantially complete, generally in less than about fifty hours, generally less than about forty hours.

When the reaction has been completed, the correlative oxide may be recovered immediately by removing the organic solvent and water as an azeotrope. Alternatively, the azeotropic mixture may be removed during the course of the reaction with additional solvent added to the reaction. The azeotropic mixture is preferably removed with the aid of a vacuum, typically of at least 25 mm of mercury, with sufficient organic solvent added to insure complete removal of the water from the hydrogen peroxide. When the correlative oxide is a tertiary amine oxide it is thus recovered as a solid in either the dihydrate, the monohydrate, and/or the anhydrous form.

The recovered correlative oxide may be utilized as collected or the purity of the correlative oxide may be improved by recrystallizing it one or more times from an organic solvent in which it can be dissolved at a higher temperature and from which it can be precipitated at a lower temperature.

Recrystallization can also be used to reduce the water content of the recovered correlative oxide, if desired, by using an organic solvent, such as ethyl acetate, in which water is at least partially soluble. For example, if the amine oxide is recovered as a dihydrate, and it is wished to convert it to an oxide containing a lesser amount of water, e.g., to a mixture of dihydrate, monohydrate, and anhydrous oxide or to the monohydrate or anhydrous form, the amine oxide can be recrystallized from such an organic solvent until the desired degree of dehydration is accomplished.

While the initial salts of the transition metals utilized as precursors for the synthesis or preparation of the non-symmetric or chiral transition metal complex will usually involve the classic counter-ions or anions such as sulfate, phosphate, halide (fluoride, chloride, bromide or iodide), nitrate, nitrite and the like it is usually more convenient in terms of subsequent reactions and the ability to separate products to utilize complex non-oxidizing anions such exemplified by $(SbF_6)^{-1}$, $(AsF_6)^{-1}$, $(PF_6)^{-1}$, or $(BF_4)^{-1}$; in some cases the organic analogs of these anions may be better choices, e.g. $(B(C_6H_5)_4)^{-1}$. These preferred salt forms for the non-symmetric or chiral transition metal complexes are easily prepared by conventional techniques of anion exchange typically employing the sodium, potassium or ammonium salts of the anions: $Na(SbF_6)$, $Na(AsF_6)$, $Na(PF_6)$, $Na(BF_4)$, $K(SbF_6)$, $K(AsF_6)$, $K(PF_6)$, $K(BF_4)$, $NH_4(SbF_6)$, $NH_4(AsF_6)$, $NH_4(PF_6)$, or $NH_4(BF_4)$.

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The skilled artisan will appreciate that pharmaceutical compositions containing active agents such as proton pump and H2 antagonists are well known in the art. Some examples of such compositions and their methods of manufacture are shown for example; in: U.S. Pat. No. 5,626,875, filed on Apr. 27, 1995, by Rodes et al. and assigned to Esteve Quimica, S.A.; U.S. Pat. No. 6,077,541, filed Jun. 18, 1999, by Chen et al., and assigned to Andrx Corporation; U.S. Pat. No. 6,869,615 entitled "Pharmaceutical formulations containing a non-steroidal anti-inflammatory drug and a proton pump inhibitor" and assigned to Andrx Corporation; U.S. Pat. No. 6,855,336 entitled "5-methoxy-2-((4-methoxy-3,5-dimethyl-2-pyridinyl)methyl)methylsulfinyl)-1H-benzimidazole formulation" and assigned to Andrx Corporation; U.S. Pat. No. 6,780,435 entitled "5-methoxy-2-((4-methoxy-3,5-dimethyl-2-pyridinyl)methyl)methylsulfinyl)-1H-benzimidazole formulation" and assigned to Andrx Corporation; U.S. Pat. No. 6,733,778 entitled "5-methoxy-2-((4-methoxy-3,5-dimethyl-2-pyridinyl)methyl)methylsulfinyl)-1H-benzimidazole formulation" and assigned to Andrx Corporation; U.S. Pat. No. 6,602,522 entitled "5-methoxy-2-((4-methoxy-3,5-dimethyl-2-pyridinyl)methyl)methylsulfinyl)-1H-benzimidazole formulation" and assigned to Andrx Corporation; U.S. Pat. No. 6,544,556 entitled "Pharmaceutical formulation for acid-labile compounds" and assigned to Andrx Corporation; U.S. Pat. No. 6,174,548 entitled "Pharmaceutical formulations containing a non-steroidal anti-inflammatory drug and a proton pump inhibitor" and assigned to Andrx Corporation; U.S. Pat. No. 6,174,548 entitled "5-methoxy-2-((4-methoxy-3,5-dimethyl-2-pyridinyl)methyl)methylsulfinyl)-1H-benzimidazole Formulation" and assigned to Andrx Corporation; U.S. Pat. No. 6,096,340 entitled "5-methoxy-2-((4-methoxy-3,5-dimethyl-2-pyridinyl)methyl)methylsulfinyl)-1H-benzimidazole Formulation" and assigned to Andrx Corporation; U.S. Pat. No. 6,077,541 entitled "5-methoxy-2-((4-methoxy-3,5-dimethyl-2-pyridinyl)methyl)methylsulfinyl)-1H-benzimidazole Formulations" and assigned to Andrx Corporation; U.S. Pat. No. 6,207,198, filed Aug. 3, 1998, by Seth Pawan and assigned to Schwarz Pharma; U.S. Pat. No. 6,248,355, entitled "Pharmaceutical Compositions Containing an Acid labile O—M—E—P—R—A—Z—O—L—E and Process for its Preparation"; and U.S. Pat. No. 4,853,230, filed Apr. 20, 1987, by Lovgren et al. and assigned to Astra Zeneca, each of which is herein incorporated by reference in their entirety as though set forth in full.

Other features of the invention will become apparent in the course of the following descriptions of exemplary embodiments which are given for illustration of the invention and are not intended to be limiting thereof.

EXAMPLES

Solution ratio express a volume relationship, unless stated otherwise. NMR chemical shifts (δ) are reported in parts per million. Abbreviations used in the Examples are defined as follows: ".degree. C." for degrees Celsius, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "HPLC" for high pressure liquid chromatography, "rt" for room temperature, "NMR" for nuclear magnetic resonance spectroscopy, "tlc" for thin layer chromatography, "atm" for atmosphere, and ".alpha.", ".beta.", "R", and "S" are stereochemical designations familiar to one skilled in the art.

Example 1

Preparation of Ruthenium Cyclopentadienyl Phosphine Complexes Materials $RuCl_3 \cdot 3H_2O$ is available from a variety a fine chemical supply houses, including for example Aldrich or Degussa.

2(S), 3(S)-bis(diphenylphosphino)butane commercially called (S,S)-CHIRAPHOS (hereinafter abbreviated "chirpp") may be obtained from Strem Chemicals and used without further purification.

The phosphine ligands dppm (1,1-bis-diphenylphosphinomethane), dppe (1,2-bis-diphenylphosphinoethane) and dpme (2-(dimethylphosphino)ethyl) diphenylphosphine are prepared according to methods referenced at footnote 16 of Schenk et al., Inorg. Chem., 1997, 36, 2372 as are the ruthenium complexes (CpRu(LL')Cl; Cp is cyclopentadienyl or cyclopentadienylide and LL' is $(PPh_3)_2$, dppm; dppe; CO; $PPh_3$, dpme or chirp.

Thioethers may be prepared by alkylation of the corresponding thiols or in some instances they may be purchased from Aldrich.

Dimethyldioxirane is used as a freshly prepared 0.08 to 0.12 M solution in acetone, as described in Adam et al., Chem. Ber., 1991, 124, 2377, or Murray et al., J. Org. Chem., 1985, 50, 2817.

Preparation of Ruthenium Thioether Complexes (CpRu(LL')Cl, 0.25 mmole, and $NH_4(PF_6)$ 0.30 mmole, and the appropriate thioether, 1.0 mmole are suspended in methanol, $CH_3OH$, and are heated to 60° C. for three hours or sixteen hours when LL' is carbonyl (CO) or triphenylphosphine ($PPh_3$). The volatiles are removed under vacuum and the residue is extracted with several portions dichloromethane, $CH_2Cl_2$. After filtering, the products are precipitated by partial evaporation and addition of diethyl ether, $(CH_3)_2O$. The thioethers used are: $CH_3SC_6H_5$, $CH_3S$-i-$C_3H_7$, $CH_3SCH_2C_6H_5$ and 5-methoxy-2-((4-methoxy-3,5-dimethyl-2-pyridinyl)methyl)methylthio)-1H-benzimidazole (pyrmetazole); the complexes prepared are (CpRu(chirp)($CH_3SC_6H_5$))($PF_6$), (CpRu(chirp)($CH_3S$-i-$C_3H_7$))($PF_6$), (CpRu(chirp)($CH_3SCH_2C_6H_5$))($PF_6$), and (CpRu(chirp)(5-methoxy-2-((4-methoxy-3,5-dimethyl-2-pyridinyl)methyl) methylthio)-1H-benzimidazole ))($PF_6$). While conversions are essentially quantitative for the methyl substituted thioethers, they are less complete for more sterically demanding substrates and attempts to drive the reaction using larger excesses of the dimethyldioxirane increases decomposition. Other oxygen sources are therefore probably more suitable as the reaction becomes more sterically demanding in terms of substituents on the complexed sulfure of the thioether.

Example 2

Oxidation of the Thioether Complexes to Produce Sulfoxide Complexes

To a solution of any of the thioether complexes formed in example 1, (0.12 mmol) in acetone (10 mL) at 0° C. is slowly added a four (4)-fold excess of a solution of dimethyldioxirane in acetone cooled to −30° C. After 45 minutes all volatiles are removed under vacuum. Yields are nearly quantitative and diastereoisomer ratios are determined from the NMR spectra of the crude reaction mixture. When liberated from the complexing transition metal cation the resulting methyl sulfoxides show a selectivity to the S enantiomeric form ranging from 73% for oxidation of the complexed methyl phenyl thioether, to 93% for the complexed methyl iso-propyl thioether, to greater than 99% for the complexed methyl benzylidene thioether.

Example 3

Recovery of the Complexed Sulfoxides Produced by Oxidation of Complexed Thioether The sulfoxide complexes (0.10 mmole), sodium iodide (NaI) (0.50 mmole) and acetone (5 nL) are heated under efflux (Reflux) for 15 hours. The mixtures are then evaporated to dryness and the residue extracted with dichloromethane (2 mL) and are chromatgraphed over a short 10 cm silica column. First the iodide complex CpRu(chirp)I is eluted and then the sulfoxides are eluted using acetone as the eluent. Evaporation of the acetone leaves the sulfoxides. When the thioether is 5-methoxy-2-((4-methoxy-3,5-dimethyl-2-pyridinyl)methyl)methylthio)-1H-benzimidazole, the recovered sulfoxide is 5-methoxy-2-((4-methoxy-3,5-dimethyl-2-pyridinyl)methyl)methylsulfinyl)-1H-benzimidazole, commonly or generically known as 5-methoxy-2-((4-methoxy-3,5-dimethyl-2-pyridinyl)methyl)methylsulfinyl)-1H-benzimidazole. The process produces the 5-methoxy-2-((4-methoxy-3,5-dimethyl-2-pyridinyl)methyl)methylsulfinyl)-1H-benzimidazole in enantiomeric excess, primarily in the S form.

Example 4

Preparation of Pharmaceutical Dosage Forms Using Benzimidizole Compounds Made According to Example 3

In 3440 g of deionized water 436 g of S-5-methoxy-2-((4-methoxy-3,5-dimethyl-2-pyridinyl)methyl)methylsulfinyl)-1H-benzimidazole, 444 g of hydroxypropyl methylcellulose and 118 g of talc are dispersed. 3010 g of inert uniform sugar/starch spheres (composition according to US Pharmacopoeia) are introduced into a fluidized bed apparatus and the previous obtained dispersion is sprayed on the spheres. After spraying, the spheres are dried before applying the second layer.

In 2365 g of deionized water, 355 g of hydroxypropylmethylcellulose, 43 g of talc and 43 g of titanium dioxide are dispersed and the resulting aqueous dispersion is sprayed on the spheres obtained in the previous step. After spraying, the spheres are dried before applying the third enteric coating layer.

In 1890 g of deionized water, 1950 g of methacrylic acid copolymer (US Pharmacopoeia, type C aqueous dispersion), 98 g of triethylcitrate and 98 g of talc are dispersed, and the resulting aqueous dispersion is sprayed on the spheres obtained in the previous step. After applying this final enteric coating layer the spheres (pellets) are dried.

Example 5

Preparation of Pharmaceutical Dosage Forms using Benzimidizole Compounds Made According to Example 3

Active pellets of 5-methoxy-2-((4-methoxy-3,5-dimethyl-2-pyridinyl)methyl)methylsulfinyl)-1H-benzimidazole are formed by placing sugar spheres in a fluidized bed coater and spraying a suspension containing 5-methoxy-2-((4-methoxy-3,5-dimethyl-2-pyridinyl)methyl)methylsulfinyl)-1H-benzimidazole onto the sugar spheres. The formulation for making the active pellets has the following composition:
povidone, USP (Plasdone K90) 4.5 g
sodium lauryl sulfate, NF 10.6 g
lactose anhydrous, NF 427.7 g
disodium phosphate, NF 51.3 g
S-5-methoxy-2-((4-methoxy-3,5-dimethyl-2-pyridinyl)methyl)methylsulfinyl)-1H-benzimidazole, USP (micronized) 427.7 g
purified water, USP 3336.0 g The povidone, lactose anhydrous, disodium phosphate and the purified water are mixed with a mechanical mixer until the materials are dissolved. Then the sodium lauryl sulfate is added to the mixture with gentle stirring to avoid the formation of excess foam until it dissolves completely. At that time the micronized s-5-methoxy-2-((4-methoxy-3,5-dimethyl-2-pyridinyl)methyl)methylsulfinyl)-1H-benzimidazole is added to the mixture and gentle stirring is continued until the micronized s-5-methoxy-2-((4-methoxy-3,5-dimethyl-2-pyridinyl)methyl)methylsulfinyl)-1H-benzimidazole is completely dispersed.

2500.0 g of non-pareil sugar spheres (USPXII) (18/20 mesh) are placed in the fluidized bed coater and the suspension containing the s-5-methoxy-2-((4-methoxy-3,5-dimethyl-2-pyridinyl)methyl)methylsulfinyl)-1H-benzimidazole is coated at a product temperature of 35-45° C.; an atomization pressure of 1.5-3.0 bar and a pump rate of 2-50 ml/minute, starting with a slow rate of pumping to avoid agglomeration and increasing the rate of pumping consistent with the avoidance of the formation of agglomerates.

After coating is complete the pellets are dried at a temperature of 50° C. until the loss on drying is less than 2.5 wt % The pellets are then screened through a #14 mesh screen and coated with the following enteric coating formulation:
hydroxypropylmethylcellulose phthalate, NF 258.1 g
cetyl alcohol, NF 12.9 g talc, USP 129.0 g
isopropyl alcohol, USP* 1663.0 g
acetone, NF* 1663.0 g
*evaporates during processing The hydroxypropylmethylcellulose phthalate and the cetyl alcohol are mixed with the isopropyl alcohol and the acetone with agitation until all of the materials are dissolved. The talc is dispersed with agitation in this solution. One kilogram of the active pellets are placed in a fluidized bed coater and all of the enteric coating mixture is applied using the coating conditions that were used to form the active pellets. The enteric coated pellets are then placed into No. "2", hard gelatin capsules containing pellets which are equivalent to 20 mg of s-5-methoxy-2-((4-methoxy-3,5-dimethyl-2-pyridinyl)methyl)methylsulfinyl)-1H-benzimidazole.

Example 6

Preparation of Pharmaceutical Dosage Forms using Benzimidizole Compounds Made According to Example 3

A pharmaceutical composition according to the present invention, in the form of micro-tablets contained in a gelatin capsule having the following composition, expressed in mg, is prepared.
Composition of Core
per capsule microtablet (times 16 tablets.)
s-5-methoxy-2-((4-methoxy-3,5-dimethyl-2-pyridinyl)methyl)methylsulfinyl)-1H-benzimidazole 1.250 (20.00)
Hydroxypropylmethylcellulose 0.625 (10.00)
Lactose 11.875 (190.00)
Sodium stearylflimarate 0.150 (2.40)
Crospovidone 0.750 (12.00)
Water 7.500 (120.00)

Composition of Intermediate Layer
Per capsule microtablet (.times. 16 tablets.)
Talc 0.375 (6.00)
Titanium dioxide 0.150 (2.40)
Hydroxypropylmethylcellulose 0.750 (12.00)
Water 5.000 (80.00)
Composition of the Enteric Layer
per per capsule microtablet (times 6 tablets.)
methacrylic acid copolymer, 1.375 (22.00)
type C triethyl citrate 0.206 (3.30)
Talc 0.275 (4.40)
Water 3.750 (60.00)

First, the core is prepared by dissolving hydroxypropylmethylcellulose in water followed by addition of the s-5-methoxy-2-((4-methoxy-3,5-dimethyl-2-pyridinyl)methyl)methylsulfinyl)-1H-benzimidazole and homogenization of the resulting suspension. The s-5-methoxy-2-((4-methoxy-3,5-dimethyl-2-pyridinyl)methyl)methylsulfinyl)-1H-benzimidazole suspension thus obtained is sprayed onto lactose nuclei having a particle size of 250 .mu.m, in a suitable fluidized bed granulator, such as a granulator sold by the companies Glatt, Aeromatic, etc. Any type of fluidized bed granulator conventionally used for this type of step can be employed with the present invention. After all the suspension is sprayed, the nuclei are dried in a conventional manner, using, for example a fluidized bed, the temperature of the product preferably remaining below 450° C. The sodium stearylfumarate and the crospovidone are than added to the dried nuclei, followed by mixing. After this, compression of the mixture obtained is carried out to obtain microtablets of a diameter of about 2.5 mm (generally comprising between 2 and 4 mm); alternatively, compression of the mixture obtained is carried out to obtain tablets of conventional dimensions. The microtablets and the tablets can contain effective amounts of the active agent of for example, 20 mg and 40 mg.

The intermediate layer which is prepared by dissolving the hydroxypropyl methylcellulose in water followed by addition of talc and titanium dioxide followed up by homogenization, is deposited by spraying onto the microtablets. This operation can be carried out in any suitable coating device that allows a regular film to be obtained, for example a Glatt coater with a Wurster type column.

Example 7

Preparation of Pharmaceutical Dosage Forms using Benzimidizole Compounds Made According to Example 3

A pharmaceutical composition according to the present invention, in the form of micro-tablets contained in a gelatin capsule having the following composition, expressed in mg, is prepared.
Uncoated Pellets
Lactose powder 253 g
I Lactose anhydrous 167 g
Hydroxypropyl cellulose 25 g
S-5-methoxy-2-((4-methoxy-3,5-dimethyl-2-pyridinyl)methyl)methylsulfinyl)-1H-benzimidazole 50 g
Sodium lauryl sulphate 5 g
II Disodium hydrogen phosphate 1.5 g
Sodium dihydrogen phosphate 0.1 g
Distilled water 125 g The dry ingredients (I) are premixed in a mixer. Addition of a granulation liquid (II) containing the suspended active compound is made and the mass is wet-mixed to a proper consistency. The wet mass is pressed through an extruder and spheronized to pellets. The pellets were dried and classified into suitable particle size ranges.
Subcoated Pellets
Uncoated pellets 500 g
III Hydroxypropyl methyl cellulose 20 g
Distilled water 400 g
The polymer solution (III) is sprayed onto the uncoated pellets in a fluidized bed apparatus. The spray guns ware placed above the fluidized bed.
Enteric Coated Pellets
Subcoated pellets 500 g
IV Hydroxypropyl methylcellulose phthalate 57 g
Cetyl alcohol 3 g
Acetone 540 g
Ethanol 231 g The polymer solution (IV) is sprayed on the subcoated pellets in a fluidized bed apparatus with spray guns placed above the bed. After drying to a water content of 0.5% the enteric coated pellets are classified and filled into hard gelatin capsules in an amount of 284 mg, corresponding to 25 mg of active compound 1. 30 capsules are packed in tight containers together with a desiccant.

Example 8

Preparation of Pharmaceutical Dosage Forms Using Benzimidizole Compounds Made According to Example 3

A pharmaceutical composition according to the present invention, in the form of micro-tablets contained in a gelatin capsule having the following composition, expressed in mg, is prepared.
Uncoated Pellets
S-5-methoxy-2-((4-methoxy-3,5-dimethyl-2-pyridinyl)methyl)methylsulfinyl)-1H-benzimidazole, sodium salt 339 g
Mannitol powder 2 422 g
I Lactose anhydrous 120 g
Hydroxypropyl cellulose 90 g
Microcrystalline cellulose 60 g
Sodium lauryl sulphate 7 g
II Distilled water 650 g The preparation is made as described in the previous example (Example 7) with the exception that the sodium salt of the s-benzimidizole compound was added together with the other ingredients in mixture I.
Subcoated Pellets
Uncoated pellets 500 g
Hydroxypropyl methylcellulose 20 g
III Aluminium hydroxide/magnesium carbonate 4 g
Distilled water 400 g
Pellets subcoated with
III 500 g Hydroxypropyl methylcellulose 20 g
IV Distilled water 400 g The two subcoat layers, III and IV, were applied to the uncoated pellets in a fluidized bed apparatus in consecutive order as previously described.
Enteric Coated Pellets
Subcoated pellets 500 g
Hydroxypropyl methylcellulose phthalate 57 g
V Cetyl alcohol 3 g
Acetone 540 g
Ethanol 231 g The preparation of enteric coated pellets was performed as described in Example 7.

Example 9

Preparation of Pharmaceutical Dosage Forms using Benzimidizole Compounds Made According to Example 3

This example gives the composition of one unit dose according to the invention.
Tablet core
S-5-methoxy-2-((4-methoxy-3,5-dimethyl-2-pyridinyl)methyl)methylsulfinyl)-1H-benzimidazole, 15 mg
Lactose 119 mg
Hydroxypropyl cellulose (low substitution) 5 mg
Hydrox$_{ypro}$pyl cellulose 1 mg (low substitution)
Talc 5 mg
Mg(OH)$_2$ 15 mg
Total 160 mg Tablet cores having the composition above and each weighing 160 mg were first made by known techniques.
Separating Layer (Inner)
Hydroxypropyl cellulose 2 mg
Synthetic hydrotalcite 0.3 mg [Al$_2$O$_3$.6MgO.CO$_2$.12H2O]
Separating Layer (Outer)
Hydroxypropyl cellulose 2 mg The two separating layers were applied to the cores by known coating techniques.
Enteric Coating Layer
Hydroxypropyl methylcellulose phthalate 7 mg
Cetyl alcohol 0.5 mg The enteric coating solution was sprayed on the cores coated by the two separating layers by known enteric coating techniques.

The foregoing examples are merely illustrative of the invention, serving to illustrate only some of the features of the present invention. The appended claims are intended to claim the invention as broadly as it has been conceived and the examples herein presented are illustrative of selected embodiments from a manifold of all possible embodiments. Accordingly it is Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied, those ranges are inclusive of all sub-ranges there between. Such ranges may be viewed as a Markush group or groups consisting of differing pairwise numerical limitations which group or groups is or are fully defined by its lower and upper bounds, increasing and/or decreasing at single integers increments from lower endpoints to upper endpoints. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims. All United States patents (and patent applications) referenced herein are herewith and hereby specifically incorporated by reference in their entirety as though set forth in full.

Having described the invention, we claim:

1. A composition of matter comprising a sulfoxide, 5-methoxy-2-((4-methoxy-3,5-dimethyl-2-pyridinyl)methyl)methylsulfinyl)-1H-benzimidazole, said sulfoxide having R and S enantiomers and further comprising a compound selected from the group consisting of a transition metal catalyst and an oxygen source wherein said transition metal catalyst is a transition metal complex wherein the transition metal of said transition metal complex is selected from the group consisting of Cr, W, Ru, Rh, Pd, Ir and Pt and wherein said oxygen source is selected from the group consisting of peracids, hydrogen peroxide, dimethyldioxirane and molecular oxygen; wherein the thioether is oxidized to a sulfoxide and has one of either the R and S enantiomers in an enantiomeric excess.

2. A composition according to claim 1, wherein the S enantiomer of the sulfoxide is present in a amount of from about 55% to about 99%.

3. A composition according to claim 1, wherein the S enantiomer of the sulfoxide is present in a amount of from about 55% to about 95%.

4. A composition according to claim 1, wherein the S enantiomer of the sulfoxide is present in a amount of from about 55% to about 90%.

5. A composition according to claim 1, wherein the S enantiomer of the sulfoxide is present in an amount of from about 55% to about 85%.

6. The composition of claim 1 wherein said transition metal complex comprises a ligand selected from the group consisting of monodentate, bidentate tridentate or polydentate ammines, di-ammines, polyamines, phosphines, di-phosphines and polyphosphines.

7. The composition of claim 1 wherein said transition metal complex is a non-symmetric coordination complex of said transition metal.

8. The composition of claim 1 wherein said transition metal complex additionally comprises cyclopentadienyl.

* * * * *